United States Patent
Chen et al.

(10) Patent No.: US 10,352,855 B2
(45) Date of Patent: Jul. 16, 2019

(54) METHOD, APPARATUS AND OPTICAL DEVICE FOR DETECTING RELATIONSHIP BETWEEN EVANESCENT FIELD AND GOOS-HANCHEN SHIFT

(71) Applicant: NANKAI UNIVERSITY, Tianjin (CN)

(72) Inventors: Ping Chen, Tianjin (CN); Ming Li, Tianjin (CN); Weiwei Liu, Tianjin (CN); Lie Lin, Tianjin (CN)

(*) Notice: Subject to any disclaimer, the term of this patent is extended or adjusted under 35 U.S.C. 154(b) by 0 days.

(21) Appl. No.: 16/048,263

(22) Filed: Jul. 28, 2018

(65) Prior Publication Data

US 2018/0364164 A1 Dec. 20, 2018

Related U.S. Application Data

(63) Continuation of application No. PCT/CN2016/077613, filed on Mar. 29, 2016.

(30) Foreign Application Priority Data

Jan. 28, 2016 (CN) .......................... 2016 1 0059996

(51) Int. Cl.
*G01N 21/552* (2014.01)
(52) U.S. Cl.
CPC .................................. *G01N 21/552* (2013.01)
(58) Field of Classification Search
None
See application file for complete search history.

(56) References Cited

U.S. PATENT DOCUMENTS 6,470,109 B1* 10/2002 Troll .................... G02B 6/3538
385/16
2007/0159633 A1 7/2007 Yin
(Continued)

FOREIGN PATENT DOCUMENTS

CN 101144726 A 3/2008
CN 101241017 A 8/2008

OTHER PUBLICATIONS

Internation Search Report of PCT/CN2016/077613, dated Oct. 24, 2016.

(Continued)

*Primary Examiner* — Michael P LaPage
(74) *Attorney, Agent, or Firm* — Oliff PLC

(57) ABSTRACT

A method, apparatus and optical device for detecting a relationship between an evanescent field and Goos-Hänchen shift, said method comprising: obtaining a potential field function of an evanescent field acting on total-reflection light according to physical meanings of a force function and the potential field function of light in the evanescent field (S101); obtaining a wave function of the perturbed total-reflection light by means of the Schrödinger equation by combining with the potential field function of the evanescent field acting on total-reflection light (S102); and comparing the wave function of the perturbed total-reflection light with a wave function of free total-reflection light with no action from the evanescent field, and determining a momentum gained by the total-reflection light under the action of the evanescent field, which is the same in nature as a momentum of the evanescent field (S103).

11 Claims, 5 Drawing Sheets

(56) References Cited

U.S. PATENT DOCUMENTS

| | | | |
|---|---|---|---|
| 2010/0065732 A1* | 3/2010 | Ye | B82Y 20/00 |
| | | | 250/281 |
| 2010/0165348 A1 | 7/2010 | Fleischer et al. | |
| 2013/0120750 A1* | 5/2013 | Zheng | G01J 4/00 |
| | | | 356/364 |
| 2014/0333930 A1 | 11/2014 | Parks | |
| 2015/0204723 A1* | 7/2015 | Zheng | G01J 4/00 |
| | | | 356/369 |
| 2017/0329127 A1* | 11/2017 | Liu | G02B 26/0816 |

OTHER PUBLICATIONS

Jacek Jakiel. et al. Quantum (not frustrated) theory of the total internal reflection as the source of the Goos-Hänchen shift.The European Physical Journal D. Oct. 2014, 68:305.

* cited by examiner

METHOD, APPARATUS AND OPTICAL DEVICE FOR DETECTING RELATIONSHIP BETWEEN EVANESCENT FIELD AND GOOS-HANCHEN SHIFT

CROSS REFERENCE TO RELATED APPLICATIONS

This application is a continuation of International Application No. PCT/CN2016/077613, filed on Mar. 29, 2016, which is based upon and claims priority to Chinese Patent Application No. 201610059996.2, filed on Jan. 28, 2016, titled "Call Notification Method and System", and the entire contents of which are incorporated herein by reference.

TECHNICAL FIELD

The present disclosure belongs to the technical field of optics, and particularly relates to a method, apparatus and optical device for detecting a relationship between an evanescent field and Goos-hänchen shift.

BACKGROUND

When light is totally reflected on the surface of a medium, electromagnetic theory analysis for light indicates that an electromagnetic field also exists in an optically thinner medium, total-reflection light generates a small shift in side direction relative to the point of incidence. Because the shift is discovered by Goos and Hanchen, the shift is called Goos-hänchen shift, G-H shift for short. Along with the discovery of the Goos-hänchen shift, the research on a Goos-hänchen shift generation mechanism becomes a hot issue.

There are two generally-accepted opinions at present: according to the opinion I, the Goos-hänchen shift is generated because different monochromatic planar light components in incident light have different reflection-induced phase shifts, and a reflected light beam is formed by superimposing of reflected planar light components, so that a longitudinal shift is generated in the reflected light beam; and according to the opinion II, generation of the Goos-hänchen shift is closely related to an evanescent field in the optically thinner medium, and according to the nature of energy flow in the evanescent field, the relationship between the Goos-hänchen shift and the energy flow in the evanescent field is derived from the view of energy conservation. However, the Goos-hänchen shift cannot be effectively regulated based on the above opinion II, so that the application of the Goos-hänchen shift in the fields of optical sensors, all-optical switches, light beam shift modulation devices, and the like is limited.

SUMMARY

Therefore, one object of the present disclosure is to provide a method, apparatus and optical device for detecting a relationship between an evanescent field and Goos-hänchen shift. The present method, apparatus and optical device can solve the problem that the Goos-hänchen shift cannot be effectively regulated, so that the application of the Goos-hänchen shift in the fields of optical sensors, all-optical switches, light beam shift modulation devices, and the like is limited.

On one hand, the present disclosure provides a method for detecting a relationship between an evanescent field and Goos-Hänchen shift, and the method comprises: obtaining a potential field function of an evanescent field acting on total-reflection light according to physical meanings of a force function and the potential field function of light in the evanescent field; obtaining a wave function of the perturbed total-reflection light by means of the Schrödinger equation by combining with the potential field function of the evanescent field acting on total-reflection light; and comparing the wave function of the perturbed total-reflection light with a wave function of free total-reflection light with no action from the evanescent field, and determining a momentum gained by the total-reflection light under the action of the evanescent field, which is the same in nature as a momentum of the evanescent field.

Further, the force function of light in the evanescent field is:

$$\vec{F} = \gamma^{-1}\left[\frac{1}{2\omega}\mathrm{Re}(\alpha)\nabla w + \mathrm{Im}(\alpha)\mathrm{Im}\vec{p}^o\right]$$

wherein $$w = \frac{\gamma}{2}\omega(|\vec{E}|^2 + |\vec{H}|^2) = w_e + w_m$$

is the energy density of an electromagnetic field; $\omega$ is an angular velocity; $\gamma = (8\pi\omega)^{-1}$ is the Gauss unit; for linearly polarized light, both the electric field and the magnetic field have the same degree of polarization, namely $\alpha_e = \alpha_m = \alpha$; $\vec{p}^o$ is an orbital momentum; $\vec{E}$ and $\vec{H}$ are respectively the amplitude of the electric field and the amplitude of the magnetic field; and $w_e$ and $w_m$ are respectively the energy density of the electric field and the energy density of the magnetic field.

Further, the potential field function of the evanescent field acting on total-reflection light is:

$$V(\vec{r}) = \vec{F} \cdot \vec{r}$$

wherein $\vec{r}$ is a position change of light in the potential field.

Further, the step of obtaining a wave function of the perturbed total-reflection light by means of the Schrödinger equation by combining with the potential field function of the evanescent field acting on total-reflection light specially comprise the following steps.

Step S11: the potential field function of the evanescent field acting on total-reflection light is designated as $V(\vec{r})$ and the wave function of the perturbed total-reflection light is designated as $\Psi(\vec{r}_1, t_1)$, and the relationship of perturbation by the evanescent field at the moment of $t_1$ is calculated by means of the Schrödinger equation as follows:

$$\left(i\hbar\frac{\partial}{\partial t_1} - H_0\right)\Psi(\vec{r}_1, t_1) = V(\vec{r}_1)\Psi(\vec{r}_1, t_2)$$

$$H_0 = \frac{\hbar^2}{2m}\nabla^2$$

wherein, $H_0$ is the Hamiltonian, m is the moving mass of light, $\vec{r}_1$ is the position vector of light, and h is the normalized Planck constant.

Step S12: a new expression formula of the potential field function $V(\vec{r})$ of the evanescent field acting on total-reflection light is obtained according to the force function $\vec{F}$ of light in the evanescent field, as follows:

$$V(\vec{r}) = \vec{F} \cdot \vec{r} = \frac{[k^{(t)}]^4}{3} n_2 [E_0^{(t)}]^2 \exp\left[\frac{2i}{h}(\vec{p}^{(t)} \cdot \vec{r})\right] \cdot r$$

wherein $\gamma=(8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p=\gamma k^{(t)}(\vec{E}\times\vec{H})$, and $\vec{E}$ and $\vec{H}$ are respectively the amplitude of the electric field and the amplitude of the magnetic field.

Step S13: the corresponding function in the Schrödinger equation is substituted with the new expression formula of the potential field function $V(\vec{r})$ of the evanescent field acting on total-reflection light to obtain the wave function $\Psi(\vec{r}_1, t_1)$ of the perturbed total-reflection light as follows:

$$\Psi = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right] - \frac{i}{h}\frac{[k^{(t)}]^4}{3} n_2 [E_0^{(t)}]^2 r \cdot \Delta t \cdot \exp\left\{\frac{i}{h}\left[(2\vec{p}^{(t)} + \vec{q})\cdot\vec{r}_1 - \frac{\vec{q}^2}{2m}\cdot t\right]\right\}$$

Further, the wave function $\Psi^{(0)}(\vec{r}_1, t_1)$ of free total-reflection light with no action from the evanescent field is as follows:

$$\Psi^{(0)}(\vec{r}_1, t_1) = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right]$$

Wherein a momentum obtaining unit is specifically for comparing the wave function $\Psi$ of the perturbed total-reflection light with the wave function $\Psi^{(0)}(\vec{r}_1, t_1)$ of free total-reflection light with no action from the evanescent field, and determining the momentum $2\vec{p}^{(t)}$ gained by the total-reflection light under the action of the evanescent field, which is the same in nature as the momentum of the evanescent field.

On the other hand, the present disclosure provides an apparatus for detecting a relationship between an evanescent field and Goos-Hänchen shift, and the apparatus comprises:

a potential field obtaining unit, for obtaining a potential field function of an evanescent field acting on total-reflection light according to physical meanings of a force function and the potential field function of light in the evanescent field;

a wave function obtaining unit, for obtaining a wave function of the perturbed total-reflection light by means of the Schrödinger equation by combining with the potential field function of the evanescent field acting on total-reflection light; and a momentum obtaining unit, for comparing the wave function of the perturbed total-reflection light with the wave function of free total-reflection light with no action from the evanescent field, and determining a momentum gained by the total-reflection light under the action of the evanescent field, which is the same in nature as a momentum of the evanescent field.

Further, the force function of light in the evanescent field is:

$$\vec{F} = \gamma^{-1}\left[\frac{1}{2\omega}\text{Re}(\alpha)\nabla w + \text{Im}(\alpha)\text{Im}\vec{p}^o\right]$$

wherein $$w = \frac{\gamma}{2}\omega\left[|\vec{E}|^2 + |\vec{H}|^2\right] = w_e + w_m$$

is the energy density of an electromagnetic field; $\omega$ is an angular velocity; $\gamma=(8\pi\omega)^{-1}$ is the Gauss unit; for linearly polarized light, both the electric field and the magnetic field have the same degree of polarization, namely $\alpha_e=\alpha_m=\alpha$; $\vec{p}^o$ is an orbital momentum; $\vec{E}$ and $\vec{H}$ are respectively the amplitude of the electric field and the amplitude of the magnetic field; and $w_e$ and $w_m$ are respectively the energy density of the electric field and the energy density of the magnetic field.

Further, the potential field function of the evanescent field acting on total-reflection light is:

$$V(\vec{r}) = \vec{F}\cdot\vec{r}$$

wherein $\vec{r}$ is a position change of light in the potential field.

Further, the wave function obtaining unit specially comprises:

a relationship building module, for designating the potential field function of the evanescent field acting on total-reflection light as $V(\vec{r})$ and the wave function of the perturbed total-reflection light as $\Psi(\vec{r}_1, t_1)$, and calculating the perturbation by the evanescent field at the moment of $t_1$ by means of the Schrödinger equation as follows:

$$\left(ih\frac{\partial}{\partial t_1} - H_0\right)\Psi(\vec{r}_1, t_1) = V(\vec{r}_1)\Psi(\vec{r}_1, t_2)$$

$$H_0 = \frac{h^2}{2m}\nabla^2$$

wherein $H_0$ is the Hamiltonian, m is the moving mass of light, $\vec{r}_1$ is the position vector of light, and h is the normalized Planck constant;

a potential field obtaining module, for obtaining a new expression formula of the potential field function $V(\vec{r})$ of the evanescent field acting on total-reflection light according to the force function $\vec{F}$ of light in the evanescent field, as follows:

$$V(\vec{r}) = \vec{F}\cdot\vec{r} = \frac{[k^{(t)}]^4}{3} n_2 [E_0^{(t)}]^2 \exp\left[\frac{2i}{h}(\vec{p}^{(t)}\cdot\vec{r})\right]\cdot r$$

wherein $\gamma=(8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p=\gamma k^{(t)}(\vec{E}\times\vec{H})$, and $\vec{E}$ and $\vec{H}$ are respectively the amplitude of the electric field and the amplitude of the magnetic field; and a wave function obtaining module, for substituting the corresponding function in the Schrödinger equation with the new expression formula of the potential field function $V(\vec{r})$ of the evanescent field acting on total-reflection light to obtain the wave function $\Psi(\vec{r}_1,t_1)$ of the perturbed total-reflection light as follows:

$$\Psi = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right] - $$

$$\frac{i}{h}\frac{[k^{(t)}]^4}{3}n_2[E_0^{(t)}]^2 r\cdot\Delta t\cdot\exp\left\{\frac{i}{h}\left[(2\vec{p}^{(t)}+\vec{q})\cdot\vec{r}_1 - \frac{\vec{q}^2}{2m}\cdot t\right]\right\}$$

Further, the wave function $\Psi^{(0)}(\vec{r}_1,t_1)$ of free total-reflection light with no action from the evanescent field is as follows:

$$\Psi^{(0)}(\vec{r}_1,t_1) = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right]$$

Wherein the momentum obtaining unit is specifically for comparing the wave function $\Psi$ of the perturbed total-reflection light with the wave function $\Psi^{(0)}(\vec{r}_1,t_1)$ of free total-reflection light with no action from the evanescent field, and determining the momentum $2\vec{p}^{(t)}$ gained by the total-reflection light under the action of the evanescent field, which is the same in nature as the momentum of the evanescent field.

On the other hand, the present disclosure provides an optical device, and the optical device comprises the apparatus for detecting a relationship between an evanescent field and Goos-Hänchen shift.

The optical device specially includes an optical sensor, an all-optical switch and a light beam shift modulation device.

The embodiment of the application has the following advantages:

the expression of the wave function of total-reflection light after the action of the evanescent field is obtained by considering the evanescent field as a perturbation to total-reflection light through the Schrödinger equation. By analyzing the wave function of total-reflection light after the action of the evanescent field, it can be concluded that under the action of the force of the evanescent field, total-reflection light gains a momentum which is the same in nature as a momentum of the evanescent field, and the momentum enables total-reflection light to generate a horizontal shift, i.e. Goos-hänchen shift, on the interface between media, so that the Goos-hänchen shift can be better regulated and well applied in fields such as optical sensors, all-optical switches, and light beam shift modulation devices.

DETAILED DESCRIPTION

In order to make the purpose, technical solutions and advantages of the prevent disclosure clearer, the present disclosure will be further illustrated in detail with the accompanying drawings and embodiments. It should be understood that the specific embodiments described herein are used only to explain rather than limiting the present disclosure.

The present disclosure will be described in detail below in combination with specific embodiments.

Embodiment I

Figure 1:
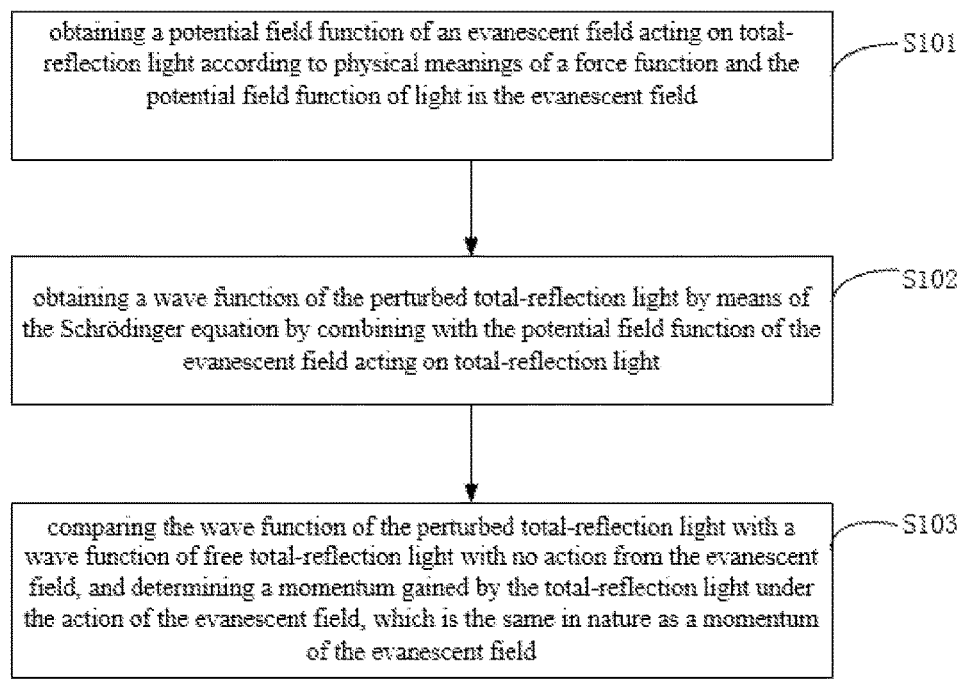
FIG. 1 is a flow chart of a method for detecting a relationship between an evanescent field and Goos-Hänchen shift provided by the embodiment I of the present disclosure.

FIG. 1 shows a realization process of a method for detecting a relationship between an evanescent field and Goos-Hänchen shift, as detailed below.

Figure 2:
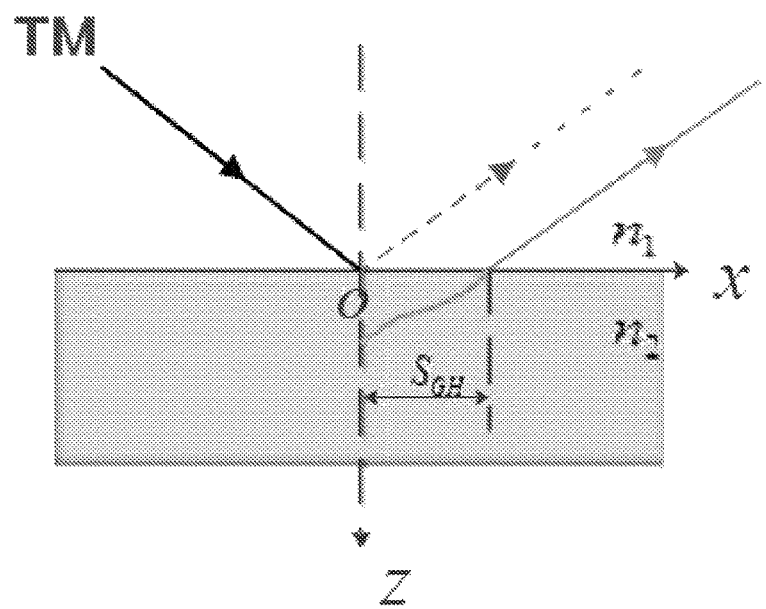
FIG. 2 is a schematic diagram of Goos-hänchen shift provided by the embodiment I of the present disclosure.

It should be noted that FIG. 2 shows a schematic diagram of the Goos-Hänchen shift. In the plane of incidence xoz, the TM planar light enters an optically thinner medium from an optically denser medium. If the angle of incidence is larger than the critical angle, total reflection will occur, and the total-reflection light beam can generate a shift, i.e. Goos-hänchen shift relative to the point of incidence, as shown in FIG. 2. For the total reflection of light on the interface between media, it can be known from the boundary conditions for electromagnetic fields that there is an electromagnetic field, i.e. an evanescent field in the optically thinner medium. Fedor I Fedorov pointed out in his paper of 2012 that the tangential energy flow of an evanescent field can generate a tangential light pressure. Afterwards, Quincke and Gall detected the presence of the force of the evanescent field through experiments. According to existing theories, the Goos-hänchen shift refers to a horizontal shift generated by total-reflection light on the interface between media due to total-reflection light obtaining a momentum under the action of the force of an evanescent field, i.e. the force of the evanescent field acts on total-reflection light to enable the total-reflection light to generate a momentum, and consequently, Goos-hänchen shift is generated.

In the step S101, a potential field function of an evanescent field acting on total-reflection light is obtained according to physical meanings of a force function and the potential field function of light in the evanescent field.

Figure 3:
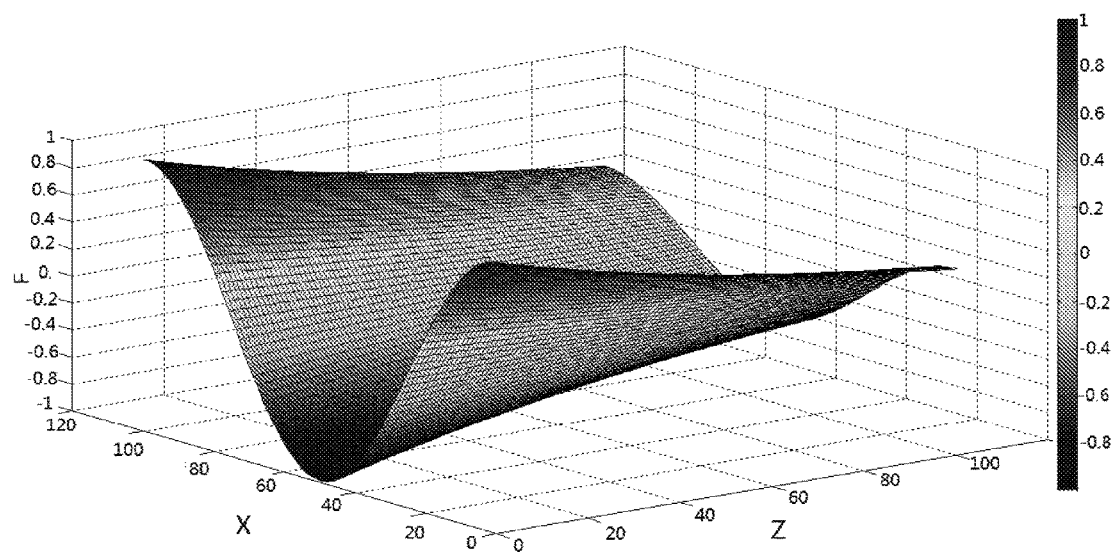
FIG. 3 is a distribution diagram of a force F of an evanescent field along with space coordinates x and z provided by the embodiment I of the present disclosure.
Figure 4:
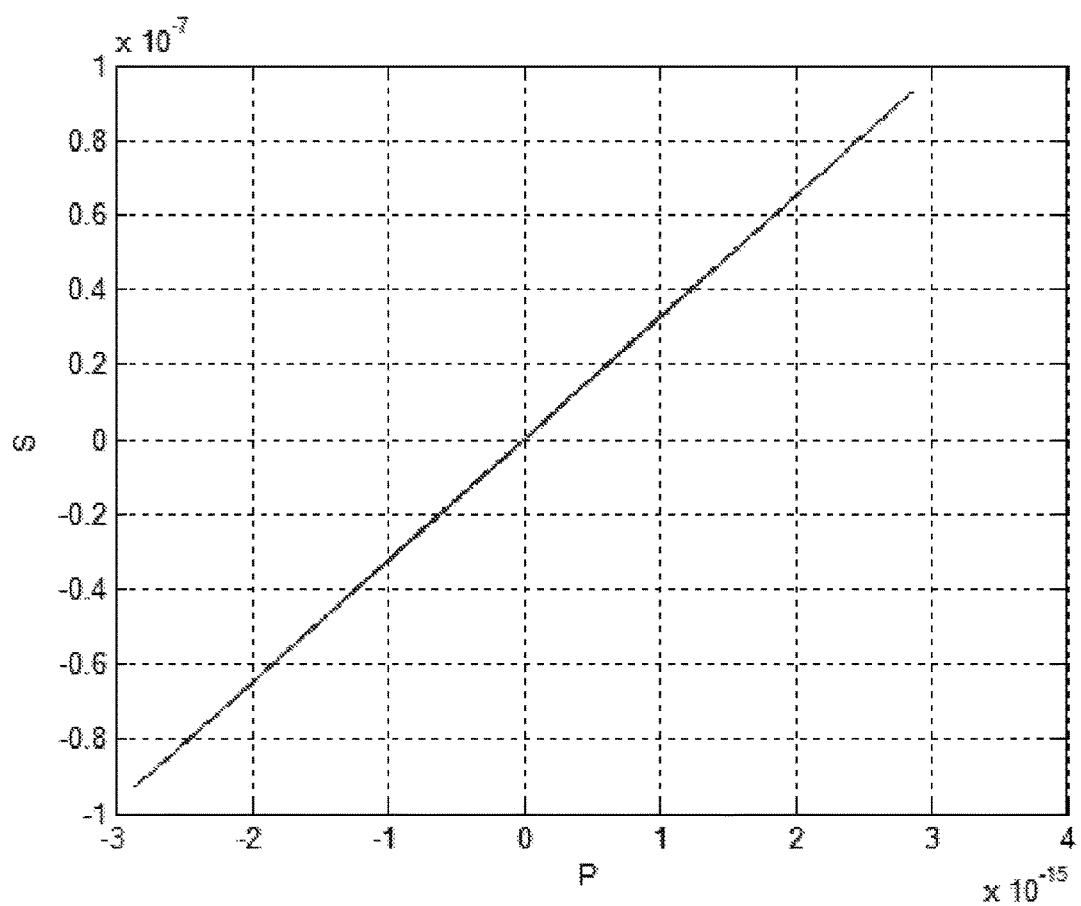
FIG. 4 is a curve graph of the relationship between Goos-hänchen shift S and a momentum P obtained by total-reflection light provided by the embodiment I of the present disclosure.
Figure 5:
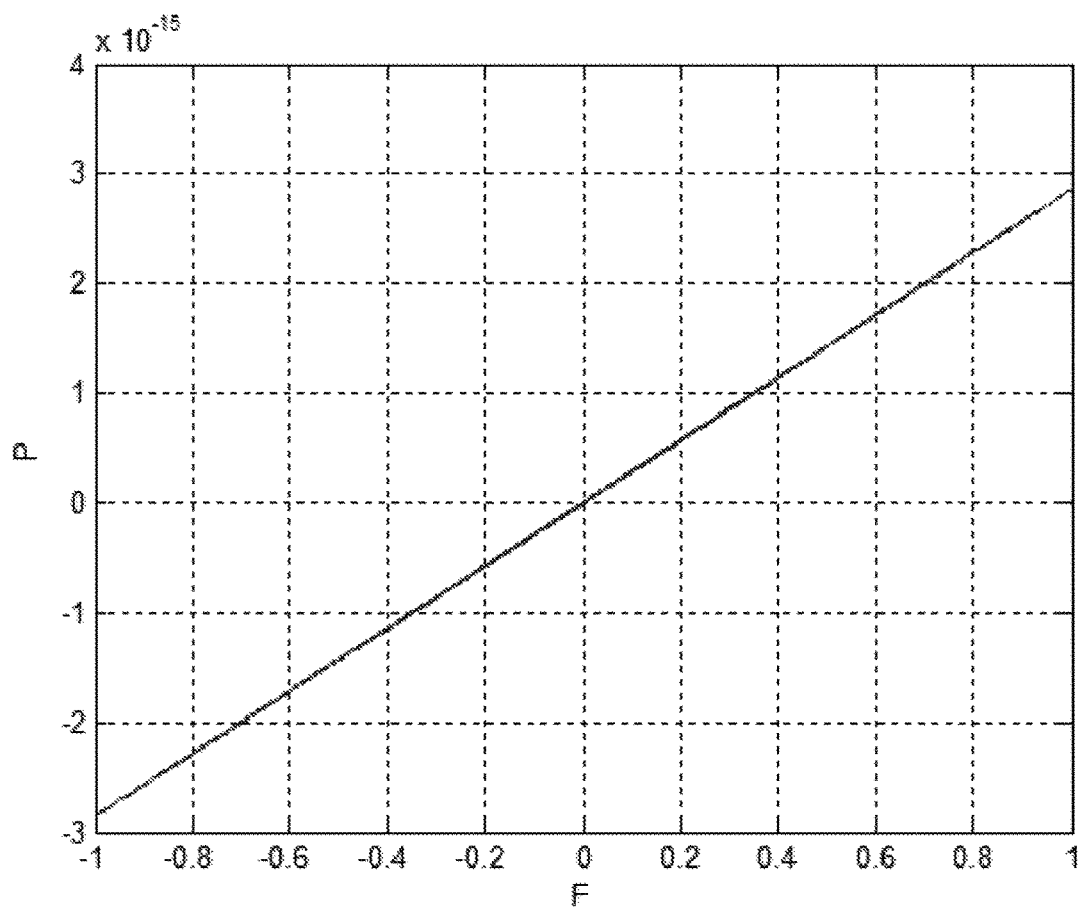
FIG. 5 is a curve graph of the relationship between a momentum P obtained by total-reflection light and a force F of an evanescent field provided by the embodiment I of the present disclosure.

In this embodiment, FIG. 3 shows a distribution diagram of a force F of an evanescent field along with space coordinates x and z. According to existing reasons for the presence of the force of the evanescent field, the force function of light in the evanescent field is:

$$\vec{F} = \gamma^{-1}\left[\frac{1}{2\omega}\mathrm{Re}(\alpha)\nabla w + \mathrm{Im}(\alpha)\mathrm{Im}\vec{p}^o\right]$$

wherein $$w = \frac{\gamma}{2}\omega(|\vec{E}|^2 + |\vec{H}|^2) = w_e + w_m$$

is the energy density of an electromagnetic field; ω is an angular velocity; $\gamma=(8\pi\omega)^{-1}$ is the Gauss unit; for linearly polarized light, both the electric field and the magnetic field have the same degree of polarization, namely $\alpha_e=\alpha_m=\alpha$; $\vec{p}^o$ is an orbital momentum; FIG. 4 shows a curve graph of the relationship between Goos-hänchen shift S and a momentum P obtained by total-reflection light, and FIG. 5 shows a curve graph of the relationship between a momentum P obtained by total-reflection light and a force F of an evanescent field; $\vec{E}$ and $\vec{H}$ are respectively the amplitude of the electric field and the amplitude of the magnetic field; and $w_e$ and $w_m$ are respectively the energy density of the electric field and the energy density of the magnetic field.

Further, the potential field function of the evanescent field acting on total-reflection light is $V(\vec{r})$, as shown below:

$$V(\vec{r}) = \vec{F} \cdot \vec{r}$$

wherein $\vec{r}$ is a position change of light in the potential field.

In the step S102, a wave function of the perturbed total-reflection light is obtained by means of the Schrödinger equation by combining with the potential field function of the evanescent field acting on total-reflection light.

In this embodiment, the evanescent field can be considered as a perturbation effect on total-reflection light when analyzed from the perspective of quantum electrodynamics. The step S102 specially comprises the following steps.

Step S11: the potential field function of the evanescent field acting on total-reflection light is designated as $V(\vec{r})$ and the wave function of the perturbed total-reflection light is designated as $\Psi(\vec{r}_1, t_1)$, and the relationship of perturbation by the evanescent field at the moment of $t_1$ is calculated by means of the Schrödinger equation as follows:

$$\left(i\hbar\frac{\partial}{\partial t_1} - H_0\right)\Psi(\vec{r}_1, t_1) = V(\vec{r}_1)\Psi(\vec{r}_1, t_1)$$

$$H_0 = \frac{\hbar^2}{2m}\nabla^2$$

wherein, $H_0$ is the Hamiltonian, m is the moving mass of light, $\vec{r}_1$ is the position vector of light, and h is the normalized Planck constant.

Step S12: a new expression formula of the potential field function $V(\vec{r})$ of the evanescent field acting on total-reflection light is obtained according to the force function $\vec{F}$ of light in the evanescent field, as follows:

$$V(\vec{r}) = \vec{F} \cdot \vec{r} = \frac{[k^{(t)}]^4}{3} n_2 [E_0^{(t)}]^2 \exp\left[\frac{2i}{\hbar}(\vec{p}^{(t)} \cdot \vec{r})\right] \cdot r$$

wherein $\gamma=(8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p=\gamma k^{(t)}(\vec{E}\times\vec{H})$, and $\vec{E}$ and $\vec{H}$ are respectively the amplitude of the electric field and the amplitude of the magnetic field.

Specially, an expression formula F of the force of the evanescent field is obtained as below, according to the force function $\vec{F}$ of light in the evanescent field:

$$F = \gamma^{-1}\frac{[k^{(t)}]^3}{3}[-\mathrm{Re}(\alpha_e\alpha_m^*)\mathrm{Re}\, p + \mathrm{Im}(\alpha_e\alpha_m^*)\mathrm{Im}p]$$

F is further derived as below:

$$F = \frac{[k^{(t)}]^4}{3} n_2 [E_0^{(t)}]^2 \exp\left[\frac{2i}{\hbar}(\vec{p}^{(t)} \cdot \vec{r})\right]$$

wherein $E_0^{(t)}$ is the initial amplitude of the evanescent field.

After the derived F is substituted into the above potential field function $V(\vec{r})$ of the evanescent field acting on total-reflection light, the following expression is obtained:

$$V(\vec{r}) = \vec{F} \cdot \vec{r} = \frac{[k^{(t)}]^4}{3} n_2 [E_0^{(t)}]^2 \exp\left[\frac{2i}{\hbar}(\vec{p}^{(t)} \cdot \vec{r})\right] \cdot r$$

Step S13: the corresponding function in the Schrödinger equation is substituted with the new expression formula of the potential field function $V(\vec{r})$ of the evanescent field acting on total-reflection light to obtain the wave function $\Psi(\vec{r}_1, t_1)$ of the perturbed total-reflection light as follows:

$$\Psi = \sqrt{\frac{1}{(2\pi\hbar)^2}} \exp\left[\frac{i}{\hbar}\left(\vec{q} \cdot \vec{r}_1 - \frac{\vec{q}^2}{2m} \cdot t\right)\right] - \frac{i}{\hbar}\frac{[k^{(t)}]^4}{3} n_2 [E_0^{(t)}]^2 r \cdot \Delta t \cdot \exp\left\{\frac{i}{\hbar}\left[(2\vec{p}^{(t)} + \vec{q}) \cdot \vec{r}_1 - \frac{\vec{q}^2}{2m} \cdot t\right]\right\}$$

In the step S103, the wave function of the perturbed total-reflection light is compared with a wave function of free total-reflection light with no action from the evanescent field, and a momentum gained by the total-reflection light under the action of the evanescent field, which is the same in nature as a momentum of the evanescent field, is determined.

In this embodiment, as shown in FIG. 2, the TM planar light beam enters the interface between media, and the plane of incidence is a two-dimensional plane. Therefore, the wave function $\Psi^{(0)}(\vec{r}_1, t_1)$ of free total-reflection light without an evanescent field is as below:

$$\Psi^{(0)}(\vec{r}_1, t_1) = \sqrt{\frac{1}{(2\pi\hbar)^2}} \exp\left[\frac{i}{\hbar}\left(\vec{q} \cdot \vec{r}_1 - \frac{\vec{q}^2}{2m} \cdot t\right)\right]$$

Wherein a momentum obtaining unit is specifically for comparing the wave function Ψ of the perturbed total-reflection light with the wave function $\Psi^{(0)}(\vec{r}_1,t_1)$ of free total-reflection light with no action from the evanescent field, and determining the momentum $2\vec{p}^{(t)}$ gained by the total-reflection light under the action of the evanescent field, which is the same in nature as the momentum of the evanescent field. That is to say, total-reflection light obtains indeed a momentum that is the same in nature as a momentum of the evanescent field under the action of the force of the evanescent field. As a result of the obtaining of such a momentum, total-reflection light moves along the interface between media and generates a horizontal shift, i.e. Goos-hänchen shift.

In this embodiment, the expression of the wave function of total-reflection light after the action of the evanescent field is obtained by considering the evanescent field as a perturbation to total-reflection light through the Schrödinger equation. By analyzing the wave function of total-reflection light after the action of the evanescent field, it can be concluded that under the action of the force of the evanescent field, total-reflection light gains a momentum which is the same in nature as a momentum of the evanescent field, and the momentum allows total-reflection light to generate a horizontal shift, i.e. Goos-hänchen shift on the interface between media, so that the Goos-hänchen shift can be better regulated and well applied in fields such as optical sensors, all-optical switches, and light beam shift modulation devices.

Embodiment II

Figure 6:
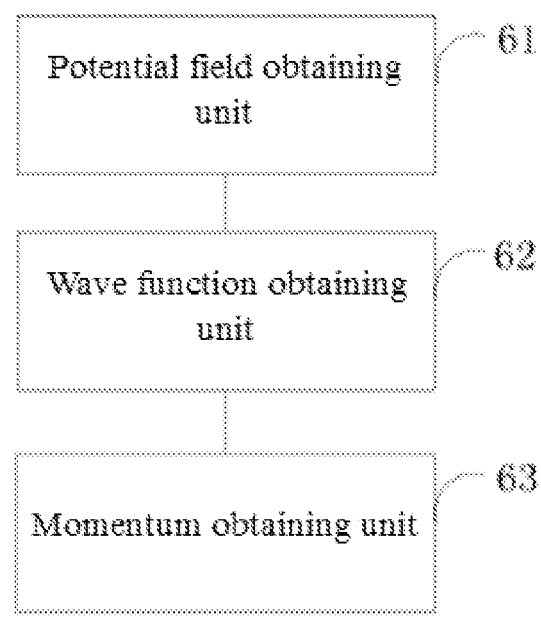
FIG. 6 is a specific structure block diagram of an apparatus for detecting a relationship between an evanescent field and Goos-hänchen shift provided by the embodiment II of the present disclosure.

FIG. 6 is a specific structure block diagram of an apparatus for detecting a relationship between an evanescent field and Goos-hänchen shift provided by the embodiment II of the present disclosure. For illustrative purposes, only the part relating to the embodiment of the present disclosure is shown. In this embodiment, the apparatus for detecting the relationship between an evanescent field and Goos-hänchen shift comprises a potential field obtaining unit 61, a wave function obtaining unit 62 and a momentum obtaining unit 63, wherein the wave function obtaining unit 62 comprises a relationship building module, a potential field obtaining module and a wave function obtaining module.

Wherein the potential field obtaining unit 61 is used for obtaining a potential field function of an evanescent field acting on total-reflection light according to physical meanings of a force function and the potential field function of light in the evanescent field;

the wave function obtaining unit 62 is used for obtaining a wave function of the perturbed total-reflection light by means of the Schrödinger equation by combining with the potential field function of the evanescent field acting on total-reflection light; and the momentum obtaining unit 63 is used for comparing the wave function of the perturbed total-reflection light with the wave function of free total-reflection light with no action from the evanescent field, and determining a momentum gained by the total-reflection light under the action of the evanescent field, which is the same in nature as a momentum of the evanescent field.

Further, the force function of light in the evanescent field is:

$$\vec{F} = \gamma^{-1}\left[\frac{1}{2\omega}\text{Re}(\alpha)\nabla w + \text{Im}(\alpha)\text{Im}\vec{p}^o\right]$$

wherein $$w = \frac{\gamma}{2}\omega(|\vec{E}|^2 + |\vec{H}|^2) = w_e + w_m$$

is the energy density of an electromagnetic field; ω is an angular velocity; $\gamma=(8\pi\omega)^{-1}$ is the Gauss unit; for linearly polarized light, both the electric field and the magnetic field have the same degree of polarization, namely $\alpha_e=\alpha_m=\alpha$; $\vec{p}^o$ is an orbital momentum; $\vec{E}$ and $\vec{H}$ are respectively the amplitude of the electric field and the amplitude of the magnetic field; and $w_e$ and $w_m$ are respectively the energy density of the electric field and the energy density of the magnetic field.

Further, the potential field function of the evanescent field acting on total-reflection light is:

$$V(\vec{r}) = \vec{F}\cdot\vec{r}$$

wherein $\vec{r}$ is a position change of light in the potential field.

Further, the wave function obtaining unit 62 specially comprises:

a relationship building module, for designating the potential field function of the evanescent field acting on total-reflection light as $V(\vec{r})$ and the wave function of the perturbed total-reflection light as $\Psi(\vec{r}_1,t_1)$, and calculating the perturbation by the evanescent field at the moment of $t_1$ by means of the Schrödinger equation as follows:

$$\left(i\hbar\frac{\partial}{\partial t_1} - H_0\right)\Psi(\vec{r}_1,t_1) = V(\vec{r}_1)\Psi(\vec{r}_1,t_1)$$

$$H_0 = \frac{\hbar^2}{2m}\nabla^2$$

wherein $H_0$ is the Hamiltonian, m is the moving mass of light, $\vec{r}_1$ is the position vector of light, and h is the normalized Planck constant;

a potential field obtaining module, for obtaining a new expression formula of the potential field function $V(\vec{r})$ of the evanescent field acting on total-reflection light according to the force function $\vec{F}$ of light in the evanescent field, as follows:

$$V(\vec{r}) = \vec{F}\cdot\vec{r} = \frac{[k^{(t)}]^4}{3}n_2[E_0^{(t)}]^2\exp\left[\frac{2i}{\hbar}(\vec{p}^{(t)}\cdot\vec{r})\right]\cdot r$$

wherein $\gamma=(8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p=\gamma k^{(t)}(\vec{E}\times\vec{H})$, and $\vec{E}$ and $\vec{H}$ are respectively the amplitude of the electric field and the amplitude of the magnetic field; and a wave function obtaining module, for substituting the corresponding function in the Schrödinger equation with the new expression formula of the potential field function $V(\vec{r})$ of the evanescent field acting on total-reflection light to obtain the wave function $\Psi(\vec{r}_1,t_1)$ of the perturbed total-reflection light as follows:

$$\Psi = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right] -$$

$$\frac{i}{h}\frac{[k^{(t)}]^4}{3}n_2[E_0^{(t)}]^2 r\cdot\Delta t\cdot\exp\left\{\frac{i}{h}\left[(2\vec{p}^{(t)}+\vec{q})\cdot\vec{r}_1 - \frac{\vec{q}^2}{2m}\cdot t\right]\right\}$$

Further, the wave function $\Psi^{(0)}(\vec{r}_1,t_1)$ of free total-reflection light with no action from the evanescent field is as follows:

$$\Psi^{(0)}(\vec{r}_1,t_1) = \sqrt{\frac{1}{(2\pi h)^2}} \exp\left[\frac{i}{h}\left(\vec{q}\cdot\vec{r}_1 - \frac{\vec{q}^2}{2m}\cdot t\right)\right]$$

Wherein the momentum obtaining unit is specifically for comparing the wave function $\Psi$ of the perturbed total-reflection light with the wave function $\Psi^{(0)}(\vec{r}_1,t_1)$ of free total-reflection light with no action from the evanescent field, and determining the momentum $2\vec{p}^{(t)}$ gained by the total-reflection light under the action of the evanescent field, which is the same in nature as the momentum of the evanescent field.

In this embodiment, the expression of the wave function of total-reflection light after the action of the evanescent field is obtained by considering the evanescent field as a perturbation to total-reflection light through the Schrödinger equation. By analyzing the wave function of total-reflection light after the action of the evanescent field, it can be concluded that under the action of the force of the evanescent field, total-reflection light gains a momentum which is the same in nature as a momentum of the evanescent field, and the momentum allows total-reflection light to generate a horizontal shift, i.e. Goos-hänchen shift on the interface between media, so that the Goos-hänchen shift can be better regulated and well applied in fields such as optical sensors, all-optical switches, and light beam shift modulation devices.

The apparatus for detecting the relationship between an evanescent field and Goos-hänchen shift provided by the embodiment of the present disclosure can be applied in the above method provided by the embodiment I. For details see the description of the above embodiment I, and this will not be repeated here.

It should be noted that the units included in the embodiments providing the apparatus are divided only by functional logic, but are not limited to such division as long as the units can achieve corresponding functions; and in addition, the specific names of various functional units are just used for distinguishing each other rather than limiting the protection scope of the present disclosure.

The embodiments in the description are described in the progressive manner, with each embodiment focusing on the difference from other embodiments. The same or similar parts among the embodiments can be referred to each other.

Although the preferred embodiments of the application have been already described, those skilled in the art can make additional changes and variations of those embodiments once they know basic innovative concepts. Therefore, the appended claims are intended to cover the preferred embodiments and all changes and variations falling within the embodiment scope of the application.

Finally, it should also be noted that relational terms such as first and second are only used to distinguish one entity or operation from another entity or operation, without necessarily requiring or implying that those entities or operations have any such actual relationship or order. Furthermore, terms such as "comprise", "include" or any other variations are intended to cover non-exclusive inclusions so that any process, apparatus, object or terminal equipment comprising a series of elements not only include those elements but also include other elements which are not explicitly listed or also include such elements as inherent in the process, apparatus, object or terminal equipment. In the case that no additional limits are present, an element restricted by the sentence "comprise a . . . " doesn't exclude that additional identical elements exist in the process, apparatus, object or terminal equipment comprising the element.

The method, apparatus and optical device for detecting the relationship between an evanescent field and Goos-hänchen shift provided by the application are introduced in detail, and the description has stated the principles and embodiments of the application with specific cases. The above embodiments are used only to help understand the apparatus and its core ideas of the application; meanwhile, those skilled in the art may make changes in terms of embodiments and the scope of application based on the ideas of the application. In sum, the content of the description should not be interpreted as limiting the application.

What is claimed is:

1. A method for detecting a relationship between an evanescent field and a Goos-Hänchen shift, the method comprising:
    obtaining a potential field function of an evanescent field acting on total-reflection light according to a force function and the potential field function of light in the evanescent field;
    obtaining a wave function of the perturbed total-reflection light by means of the Schrödinger equation by combining with the potential field function of the evanescent field acting on the total-reflection light; and
    comparing the wave function of the perturbed total-reflection light with a wave function of free total-reflection light with no interaction from the evanescent field, and determining a momentum gained by the total-reflection light under the action of the evanescent field, which is the same in nature as a momentum of the evanescent field.

2. The method according to claim 1, characterized in that the force function of light in the evanescent field is:

$$\vec{F} = \gamma^{-1}\left[\frac{1}{2\omega}\text{Re}(\alpha)\nabla w + \text{Im}(\alpha)\text{Im}\vec{p}^o\right]$$

wherein, $$w = \frac{\gamma}{2}\omega(|\vec{E}|^2 + |\vec{H}|^2) = w_e + w_m$$

is the energy density of an electromagnetic field; $\omega$ is an angular velocity; $\gamma=(8\pi\omega)^{-1}$ the Gauss unit; for linearly polarized light, both the electric field and the magnetic field have the same degree of polarization, namely $\alpha_e=\alpha_m=\alpha$; $\vec{P}^o$ is an orbital momentum; $\vec{E}$ and $\vec{H}$ are respectively the amplitude of the electric field and the amplitude of the magnetic field; $w_e$ and $w_m$ are respectively the energy density of the electric field and the energy density of the magnetic field.

3. The method according to claim 2, characterized in that the potential field function of the evanescent field acting on the total-reflection light is:

$$V(\vec{r}) = \vec{F} \cdot \vec{r}$$

wherein $\vec{r}$ a position change of light in the potential field.

4. The method according to claim 3, characterized in that the step of obtaining the wave function of the perturbed total-reflection light by means of the Schrödinger equation by combining with the potential field function of the evanescent field acting on the total-reflection light specifically comprises:

designating the potential field function of the evanescent field acting on the total-reflection light as $V(\vec{r})$ and the wave function of the perturbed total-reflection light as $\Psi(\vec{r}_1, y_1)$, and calculating the relationship of the perturbation by the evanescent field at the moment of $t_1$ by means of the Schrödinger equation as follows:

$$\left(i\hbar\frac{\partial}{\partial t_1} - H_0\right)\Psi(\vec{r}_1, t_1) = V(\vec{r}_1)\Psi(\vec{r}_1, t_1)$$

$$H_0 = \frac{\hbar^2}{2m}\nabla^2$$

wherein, $H_0$ is the Hamiltonian, m is the moving mass of light, $\vec{r}_1$ is the position vector of light, and h is the normalized Planck constant;

obtaining a new expression formula of the potential field function $V(\vec{r})$ of the evanescent field acting on the total-reflection light according to the force function $\vec{F}$ of the light in the evanescent field, as follows:

$$V(\vec{r}) = \vec{F} \cdot \vec{r} = \frac{[k^{(t)}]^4}{3}n_2[E_0^{(t)}]^2 \exp\left[\frac{2i}{\hbar}(\vec{p}^{(t)} \cdot \vec{r})\right] \cdot r$$

wherein, $\gamma = (8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p = \gamma k^{(t)}(\vec{E} \times \vec{H})$, and $\vec{E}$ and $\vec{H}$ are respectively the amplitude of the electric field and the amplitude of the magnetic field; and substituting the corresponding function in the Schrödinger equation with the new expression formula of the potential field function $V(\vec{r})$ of the evanescent field acting on the total-reflection light to obtain the wave function $\Psi(\vec{r}_1, t_1)$ of the perturbed total-reflection light as follows:

$$\Psi = \sqrt{\frac{1}{(2\pi\hbar)^2}} \exp\left[\frac{i}{\hbar}\left(\vec{q} \cdot \vec{r}_1 - \frac{\vec{q}^2}{2m} \cdot t\right)\right] -$$

$$\frac{i}{\hbar}\frac{[k^{(t)}]^2}{3}n_2[E_0^{(t)}]^2 r \cdot \Delta t \cdot \exp\left\{\frac{i}{\hbar}\left[(2\vec{p}^{(t)} + \vec{q}) \cdot \vec{r} - \frac{\vec{q}^2}{2m} \cdot t\right]\right\}.$$

5. The method according to claim 4, characterized in that, the wave function $\Psi^{(0)}(\vec{r}_1, t_1)$ of the free total-reflection light with no interaction from the evanescent field is as follows:

$$\Psi^{(0)}(\vec{r}_1, t_1) = \sqrt{\frac{1}{(2\pi\hbar)^2}} \exp\left[\frac{i}{\hbar}\left(\vec{q} \cdot \vec{r}_1 - \frac{\vec{q}^2}{2m} \cdot t\right)\right]$$

wherein a processor is specifically used for comparing the wave function $\psi$ of the perturbed total-reflection light with the wave function $\Psi^{(0)}(\vec{r}_1, t_1)$ of the free total-reflection light with no interaction from the evanescent field, and determining the momentum $2\vec{p}^{(t)}$ gained by the total-reflection light under the action of the evanescent field, which is the same in nature as the momentum of the evanescent field.

6. An apparatus for detecting a relationship between an evanescent field and a Goos-Hänchen shift, the apparatus comprising:

a processor programmed to
  obtain a potential field function of an evanescent field acting on total-reflection light according to a force function and the potential field function of light in the evanescent field;
  obtain a wave function of the perturbed total-reflection light by means of the Schrödinger equation by combining with the potential field function of the evanescent field acting on the total-reflection light; and
  compare the wave function of the perturbed total-reflection light with a wave function of the free total-reflection light with no interaction from the evanescent field, and determine a momentum gained by the total-reflection light under the action of the evanescent field, which is the same in nature as a momentum of the evanescent field.

7. The apparatus according to claim 6, characterized in that, the force function of light in the evanescent field is:

$$\vec{F} = \gamma^{-1}\left[\frac{1}{2\omega}\text{Re}(\alpha)\nabla w + \text{Im}(\alpha)\text{Im}\vec{p}^o\right]$$

wherein $$w = \frac{\gamma}{2}\omega(|\vec{E}|^2 + |\vec{H}|^2) = w_e + w_m$$

the energy density of the electromagnetic field; $\omega$ is an angular velocity, $\gamma = (8\pi\omega)^{-1}$ is the Gauss unit; for linearly polarized light, both the electric field and the magnetic field have the same degree of polarization, namely $\alpha_e = \alpha_m = \alpha$; $\vec{p}^o$ is an orbital momentum; $\vec{E}$ and $\vec{H}$ are respectively the amplitude of the electric field and the amplitude of the magnetic field; and $w_e$ and $w_n$ are respectively the energy density of the electric field and the energy density of the magnetic field.

8. The apparatus according to claim 7, characterized in that, the potential function of the evanescent field acting on the total-reflection light is:

$$V(\vec{r}) = \vec{F} \cdot \vec{r}$$

wherein $\vec{r}$ is a position change of light in the potential field.

9. The apparatus according to claim 8, characterized in that, the processor is further programmed to designate the potential field function of the evanescent field acting on the total-reflection light as $V(\vec{r})$ and the wave function of the perturbed total-reflection light as $\Psi(\vec{r}_1,t_1)$, and calculate the perturbation by the evanescent field at the moment of $t_1$ by means of the Schrödinger equation as follows:

$$\left(i\hbar\frac{\partial}{\partial t_1} - H_0\right)\Psi(\vec{r}_1, t_1) = V(\vec{r}_1)\Psi(\vec{r}_1, t_1)$$

$$H_0 = \frac{\hbar^2}{2m}\nabla^2$$

wherein $H_0$ is the Hamiltonian, m is the moving mass of light, $\vec{r}_1$ is the position vector of light, and h is the normalized Planck constant;

obtain a new expression formula of the potential field function $V(\vec{r})$ of the evanescent field acting on the total-reflection light according to the force function $\vec{F}$ of light in the evanescent field, as follows:

$$V(\vec{r}) = \vec{F}\cdot\vec{r} = \frac{[k^{(t)}]^4}{3}n_2[E_0^{(t)}]^2\exp\left[\frac{2i}{\hbar}(\vec{p}^{(t)}\cdot\vec{r})\right]\cdot r$$

wherein $\gamma=(8\pi\omega)^{-1}$ is the Gauss unit, $\alpha_e$ and $\alpha_m$ are respectively the degree of polarization of the electric field and the degree of polarization of the magnetic field, $k^{(t)}$ is the wave number of the evanescent field, $p=\gamma k^{(t)}(\vec{E}\times\vec{H})$, and $\vec{E}$ and $\vec{H}$ are respectively the amplitude of the electric field and the amplitude of the magnetic field; and substitute the corresponding function in the Schrödinger equation with the new expression formula of the potential field function $V(\vec{r})$ of the evanescent field acting on the total-reflection light to obtain the wave function $\Psi(\vec{r}_1,t_1)$ of the perturbed total-reflection light as follows:

$$\Psi = \sqrt{\frac{1}{(2\pi\hbar)^2}}\exp\left[\frac{i}{\hbar}\left(\vec{q}\cdot\vec{r}_1 - \frac{\vec{q}^2}{2m}\cdot t\right)\right] - \frac{i}{\hbar}\frac{[k^{(t)}]^2}{3}n_2[E_0^{(t)}]^2 r\cdot\Delta t\cdot\exp\left\{\frac{i}{\hbar}\left[(2\vec{p}^{(t)}+\vec{q})\cdot\vec{r} - \frac{\vec{q}^2}{2m}\cdot t\right]\right\}.$$

10. The apparatus according to claim 9, characterized in that, the wave function $\Psi^{(0)}(\vec{r}_1,t_1)$ of the free total-reflection light with no interaction from the evanescent field is as follows:

$$\Psi^{(0)}(\vec{r}_1, t_1) = \sqrt{\frac{1}{(2\pi\hbar)^2}}\exp\left[\frac{i}{\hbar}\left(\vec{q}\cdot\vec{r}_1 - \frac{\vec{q}^2}{2m}\cdot t\right)\right]$$

wherein the processor is programmed to compare the wave function $\psi$ of the perturbed total-reflection light with the wave function $\Psi^{(0)}(\vec{r}_1,t_1)$ of the free total-reflection light with no interaction from the evanescent field, and to determine the momentum $2\vec{p}^{(t)}$ gained by the total-reflection light under the action of the evanescent field, which is the same in nature as the momentum of evanescent field.

11. An optical device comprising:
the apparatus for detecting the relationship between an evanescent field and Goos-Hänchen shift according to claim 6; and
at least one of an optical sensor, a biosensor, an all-optical switch and a light beam shift modulation device for use with the apparatus for detecting the relationship between an evanescent field and Goos-Hänchen shift.

* * * * *